United States Patent
Jackson et al.

(10) Patent No.: US 11,403,862 B2
(45) Date of Patent: *Aug. 2, 2022

(54) DEEP LEARNING AUTOMATED DERMATOPATHOLOGY

(71) Applicant: PROSCIA INC., Haverford, PA (US)

(72) Inventors: Brian H. Jackson, Poquoson, VA (US); Coleman C. Stavish, Havertown, PA (US)

(73) Assignee: PROSCIA INC., Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/656,033

(22) Filed: Oct. 17, 2019

(65) Prior Publication Data

US 2020/0050832 A1 Feb. 13, 2020

Related U.S. Application Data

(63) Continuation of application No. 15/923,525, filed on Mar. 16, 2018, now Pat. No. 10,460,150.

(51) Int. Cl.

| | |
|---|---|
| G06K 9/00 | (2022.01) |
| G06V 20/69 | (2022.01) |
| G06K 9/62 | (2022.01) |
| G06T 7/00 | (2017.01) |
| G16H 30/40 | (2018.01) |
| G06N 3/08 | (2006.01) |

(52) U.S. Cl.
CPC ........... *G06V 20/698* (2022.01); *G06K 9/627* (2013.01); *G06N 3/08* (2013.01); *G06T 7/0014* (2013.01); *G06V 20/695* (2022.01); *G16H 30/40* (2018.01); *G06T 2207/20081* (2013.01); *G06T 2207/30024* (2013.01); *G06T 2207/30088* (2013.01)

(58) Field of Classification Search
CPC .. G06K 9/00147; G06K 9/0014; G06K 9/627; G06N 3/08; G16H 30/40; G06T 7/0014; G06T 2207/30024; G06T 2207/20081; G06T 2207/30088
See application file for complete search history.

(56) References Cited

U.S. PATENT DOCUMENTS

| | | | | |
|---|---|---|---|---|
| 10,003,483 B1* | 6/2018 | Migliori | ............... | G06N 3/0454 |
| 10,460,150 B2* | 10/2019 | Jackson | ............... | G06K 9/0014 |
| 2004/0264749 A1* | 12/2004 | Skladnev | ............. | A61B 5/0059 |
| | | | | 382/128 |

(Continued)

*Primary Examiner* — Tom Y Lu
(74) *Attorney, Agent, or Firm* — MH2 Technology Law Group LLP (57) ABSTRACT

Techniques for classifying a human cutaneous tissue specimen are presented. The techniques may include obtaining a computer readable image of the human tissue sample and preprocessing the image. The techniques may include applying a trained deep learning model to the image to label each of a plurality of image pixels with at least one probability representing a particular diagnosis, such that a labeled plurality of image pixels is obtained. The techniques can also include applying a trained discriminative classifier to contiguous regions of pixels defined at least in part by the labeled plurality of image pixels to obtain a specimen level diagnosis, where the specimen level diagnosis includes at least one of: basal cell carcinoma, dermal nevus, or seborrheic keratosis. The techniques can include outputting the specimen level diagnosis.

16 Claims, 7 Drawing Sheets

(56) References Cited

U.S. PATENT DOCUMENTS

| | | | |
|---|---|---|---|
| 2011/0054298 A1 | 3/2011 | Stamnes et al. | |
| 2011/0301441 A1 | 12/2011 | Bandic et al. | |
| 2012/0008838 A1* | 1/2012 | Guyon | G06T 7/0012 |
| | | | 382/128 |
| 2016/0253466 A1 | 9/2016 | Agaian et al. | |
| 2017/0287134 A1* | 10/2017 | Abedini | G06T 7/187 |
| 2018/0315506 A1* | 11/2018 | Mukhopadhyay | G16H 30/20 |

\* cited by examiner

DEEP LEARNING AUTOMATED DERMATOPATHOLOGY

CROSS-REFERENCE TO RELATED APPLICATIONS

This application is a continuation of, and claims the benefit of and priority to U.S. patent application Ser. No. 15/923,525, filed Mar. 16, 2018, the disclosure of which is hereby incorporated herein by reference in its entirety.

FIELD

This disclosure relates generally to machine learning and dermatopathology.

BACKGROUND

Pathologists routinely use microscopes to assess patterns in tissue samples on glass slides. The assessment of these patterns, which may indicate the presence of malignancies, for example, is often critical to the diagnosis of disease in humans and animals. Because human observers conduct such assessments, they are subjective. Subjectivity in diagnosis can lead to misdiagnosis, which negatively impact patients, care providers, and payers.

Specialized instruments called whole-slide scanners can capture an image of the tissue sample on a glass slide that has resolution and clarity equivalent to that provided by a microscope. Whole slide scanners output whole-slide images that can be viewed on a computer workstation and analyzed by software.

Some machine learning techniques are trained by thousands (or more) of examples of categories for classifying new data. Once trained and given new data for classification, such techniques can classify the new data, e.g., by specifying a constituent class or providing probabilities of membership in each class.

SUMMARY

According to various embodiments, an at least partially computer implemented method of classifying a human cutaneous tissue specimen is presented. The method includes obtaining a computer readable image of the human tissue sample; preprocessing the image; applying a trained deep learning model to the image to label each of a plurality of image pixels with at least one probability representing a particular diagnosis, such that a labeled plurality of image pixels is obtained; applying a trained discriminative classifier to contiguous regions of pixels defined at least in part by the labeled plurality of image pixels to obtain a specimen level diagnosis, where the specimen level diagnosis includes at least one of: basal cell carcinoma, dermal nevus, or seborrheic keratosis; and outputting the specimen level diagnosis.

Various optional features of the above embodiments include the following. The method may include receiving a confirming diagnosis from a human operator; and providing, automatically, the specimen level diagnosis to an electronic medical record system in response to the receiving the confirming diagnosis. The outputting the specimen level diagnosis may further include causing the image of the human tissue sample to be displayed to the human operator contemporaneously with the specimen level diagnosis. The applying the trained discriminative classifier to the contiguous regions of pixels defined at least in part by the labeled plurality of image pixels may further include obtaining a confidence level in the specimen level diagnosis, the method further including: determining that the confidence level exceeds a predetermined threshold; and providing the specimen level diagnosis to an electronic medical record system in response to the determining. The method may include causing a heat map representing the labeled plurality of image pixels to be displayed. The trained deep learning model may include a convolutional neural network. The method may include training the trained deep learning model using stochastic graded descent with momentum. The trained discriminative classifier may include a support vector machine. The method may include training the trained discriminative classifier using a set of vectors derived from contiguous regions identified in images by the trained deep learning model. The preprocessing may include detecting and isolating image regions that represent tissue.

According to various embodiments, a system for classifying a human cutaneous tissue specimen is presented. The system includes at least one electronic processor that executes instructions to perform operations including: obtaining a computer readable image of the human tissue sample; preprocessing the image; applying a trained deep learning model to the image to label each of a plurality of image pixels with at least one probability representing a particular diagnosis, such that a labeled plurality of image pixels is obtained; applying a trained discriminative classifier to contiguous regions of pixels defined at least in part by the labeled plurality of image pixels to obtain a specimen level diagnosis, where the specimen level diagnosis includes at least one of: basal cell carcinoma, dermal nevus, or seborrheic keratosis; and outputting the specimen level diagnosis.

Various optional features of the above embodiments include the following. The operations may further include: receiving a confirming diagnosis from a human operator; and providing, automatically, the specimen level diagnosis to an electronic medical record system in response to the receiving the confirming diagnosis. The outputting the specimen level diagnosis may further include causing the image of the human tissue sample to be displayed to the human operator contemporaneously with the specimen level diagnosis. The applying the trained discriminative classifier to the contiguous regions of pixels defined at least in part by the labeled plurality of image pixels may further include obtaining a confidence level in the specimen level diagnosis, where the operations further include: determining that the confidence level exceeds a predetermined threshold; and providing the specimen level diagnosis to an electronic medical record system in response to the determining. The operations may further include causing a heat map representing the labeled plurality of image pixels to be displayed. The trained deep learning model may include a convolutional neural network. The operations may further include training the trained deep learning model using stochastic graded descent with momentum. The trained discriminative classifier may include a support vector machine. The operations may further include training the trained discriminative classifier using a set of vectors derived from contiguous regions identified in images by the trained deep learning model. The preprocessing may include detecting and isolating image regions that represent tissue.

BRIEF DESCRIPTION OF THE DRAWINGS

Various features of the examples can be more fully appreciated, as the examples become better understood with reference to the following detailed description, when considered in connection with the accompanying figures, in which.

DETAILED DESCRIPTION

Reference will now be made in detail to the disclosed examples, which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific examples. These examples are described in sufficient detail to enable those skilled in the art to practice them and it is to be understood that other examples may be utilized and that changes may be made without departing from the scope of the disclosure. The following description is, therefore, merely exemplary.

According to some embodiments, whole slide images of human tissue are prepared, processed, and evaluated for disease using machine learning. This type of process leads to a new type of diagnostic workflow, which is at least partially reliant on such computerized information. The involvement of humans in arriving at a diagnosis may be reduced or eliminated, according to some embodiments, resulting in a fully autonomous diagnosis rendered by an image analysis system.

Some embodiments use ground truth representations of various disease and normal states to train a convolutional neural network. Outputs from the convolutional neural network are used to train a support vector machine, which subsequently provides an output diagnosis. In use, the trained convolutional neural network is applied to a new whole slide image to assign disease probabilities to each pixel. This data is then further processed and submitted to the trained support vector machine, which produces an output diagnosis. Depending on the confidence attributed to the diagnosis by the support vector machine, the output diagnosis may be acted upon, or vetted by a human before being acted upon.

Some embodiments provide automated techniques for conducting dermatopathology. Because dermatopathology is an image-intense art, and because low power recognition is often significant for accurate diagnosis, application of machine learning to cutaneous whole slide images as disclosed allows for computer assisted diagnosis. Disclosed embodiments may diagnosis basal cell carcinoma, dermal nevus, and/or seborrheic keratosis. These and other features are described in detail herein.

Figure 1:
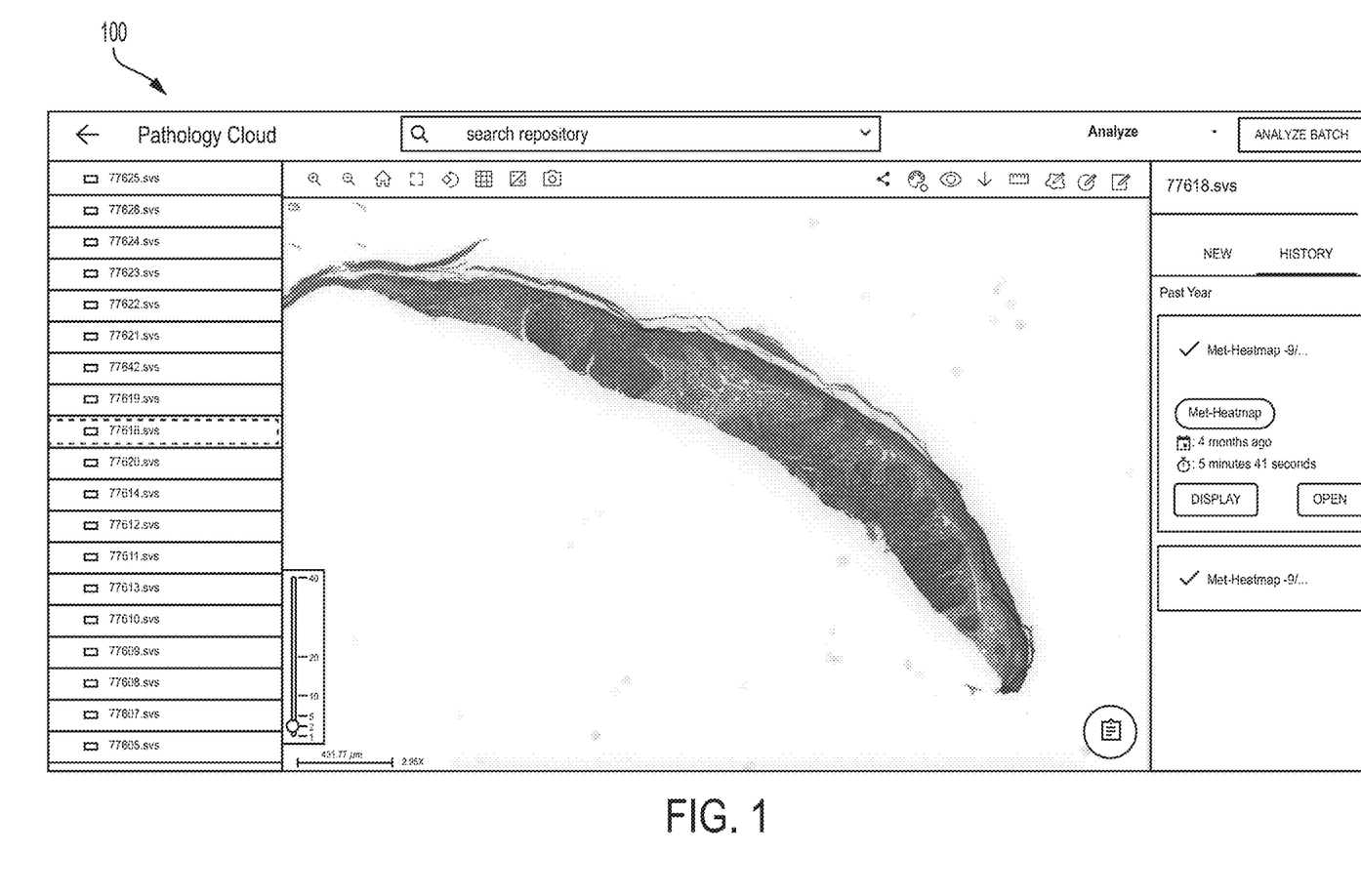
FIG. 1 depicts a scanned whole slide image of a human dermatopathological section according to various embodiments.

FIG. 1 depicts a whole slide image 100, scanned from a human dermatopathological section, according to various embodiments. Such an image 100 may be obtained from a formalin-fixed, paraffin embedded cutaneous human specimen once it is sectioned onto glass slides and stained using hematoxylin and eosin. Once physically processed as described, the glass slides are scanned using a whole-slide scanner to produce whole slide images. Some embodiments utilize machine learning to analyze a whole slide image and output a suggested dermatological diagnosis.

Figure 2:
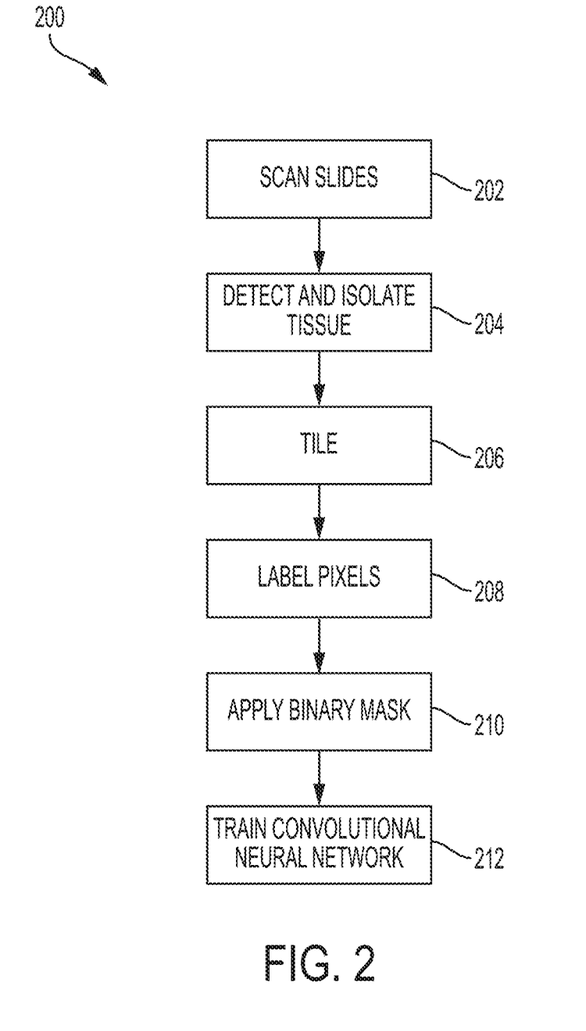
FIG. 2 is a flowchart for a method of training a deep learning model according to various embodiments.

FIG. 2 is a flowchart for a method 200 of training a deep learning model according to various embodiments. Method 200 may be implemented using a hardware computer system as shown and described below in reference to FIG. 7. Method 200 may be used to train a convolutional neural network as part of a full embodiment, e.g., as shown and described in reference to FIGS. 6 and 7, below. In particular, embodiments may utilize one or more fully convolutional neural networks, trained to assign probabilities of various diseases to each pixel in each whole-slide image. Multiple such neural networks may be trained and utilized, e.g., one per disease.

Per block 202, method 200 scans dermatological slides to obtain computer readable whole slide images. In general, specialized instruments called whole-slide scanners can capture an image of a tissue sample on a glass slide that has resolution and clarity equivalent to that provided by a microscope. Whole slide image 100 of FIG. 1 represents an example. The types of samples represented depend on the disease at issue. Example sets of sample types for various diagnostic aims are described presently.

The inventors conducted three sequential studies, to include training and testing of each individual machine learning technique and to allow for assessment and correction of design elements. All hematoxylin and eosin stained glass slides used in the studies were de-identified of patient information before scanning into whole slide images.

In the first study, a training set of 200 previously diagnosed nodular basal cell carcinoma glass slides and 100 distractor glass slides were de-identified and scanned into whole slide images at 40× magnification (using an Aperio AT2 Scanscope Console, available from Leica Biosystems). The distractor set for nodular basal cell carcinoma consisted of twenty slides each of verruca vulgaris, actinic keratoses, spongiotic dermatitis, squamous acanthomas and dermal nevi. These five distractor diagnoses were selected to include common neoplasms and an inflammatory condition.

In the second study, the training set was 125 previously diagnosed dermal nevi glass slides and 100 distractor glass slides, 20 slides each of fibroepithelial polyps, granuloma annulare, verruca vulgaris, dermatofibromas and nodular basal cell carcinomas. All de-identified glass slides were scanned into whole slide images at 40× magnification.

In the third study, 125 previously diagnosed seborrheic keratoses glass slides and 100 distractor glass slides, twenty slides each of superficial basal cell carcinomas, molluscum contagiosum, lichenoid keratoses, Bowen's disease, and verruca vulgaris, were de-identified and scanned into whole slide images at 40× magnification.

For each neural netowork, randomly selected new test sets of hematoxylin and eosin stained previously diagnosed slides, consisting of approximately 70% lesion of whole slide images and 30% distractors, were de-identified, scanned at 40× magnification into whole slide images, and uploaded into cloud storage. Table I below shows total number and diagnoses of whole slide images used for training and testing the algorithms.

TABLE 1

Number and Type of Whole Slide Images Used in Test Cases

| Diagnostic Goal | Training Set | Test Set |
|---|---|---|
| Basal Cell Carcinoma, Nodular | 200 Basal Cell Carcinoma, Nodular | 83 Basal Cell Carcinoma, Nodular |
| | 20 Verruca Vulgaris | 8 Verruca Vulgaris |
| | 20 Actinic Keratosis | 9 Actinic Keratosis |
| | 20 Spongiotic Dermatitis | 8 Spongiotic Dermatitis |
| | 20 Basosquamous Acanthoma | 7 Basosquamous Acanthoma |
| | 20 Dermal Nevis | 9 Dermal Nevis |
| Dermal Nevis | 125 Dermal Nevis | 79 Dermal Nevis |
| | 20 Fibroepithelial Polyp | 6 Fibroepithelial Polyp |
| | 20 Granuloma Annulare | 7 |
| | 20 | 8 |
| | 20 | 8 |
| | 20 | 6 |
| Seborrheic Keratosis | 125 Seborrheic Keratosis | 83 Seborrheic Keratosis |
| | 20 Verruca Vulgaris | 8 Verruca Vulgaris |
| | 20 Bowen's Disease | 8 Bowen's Disease |
| | 20 Lichenoid Keratosis | 8 Lichenoid Keratosis |
| | 20 Mollescum Contagiosum | 8 Mollescum Contagiosum |
| | 20 Basal Cell Carcinoma, Superficial | 8 Basal Cell Carcinoma, Superficial |

Thus, for each individual dermatological diagnosis, corresponding positive and negative image sets were preprocessed and decomposed to extract features relevant to the differential diagnosis.

Note that the actions of block 402 are optional in some embodiments. Instead, some embodiments may retrieve electronically stored whole slide images that have been scanned by a different entity. Method 100 may access the whole slide images by retrieving them from a remote server over a network such as the internet, for example.

Per block 204, method 200 detects and isolates image portions that show tissue. Whole slide images, containing available resolutions from 1× to 40× magnification, contained on average over 70% unnecessary background space which slowed down image processing; therefore, tissue samples on whole slide images were detected and isolated.

Per block 206, method 200 tiles the whole slide images. That is, the actions of block 206 represent each whole slide image as a plurality of overlapping tiles. The actions of this block can lead to greatly enhanced efficiency according to some embodiments. In particular, tiling the whole slide images by partitioning them into multiple tiles allows systems to perform the actions of blocks 208, 210, and 212 in parallel, using specialized computing hardware, e.g., Graphical Processing Units ("GPUs"). In particular, the actions of block 208, 210, and 212 may be performed in parallel at the tile level, rather than at the slide level. Beyond parallelization, tiling also helps prevent memory errors caused by complex computation, and achieve more than thirty times speedup on any given algorithm. In particular, medical images such as whole slide images encode massive amounts of heterogeneity due to, for example, tissue types, scanning variability and staining artifacts. Splitting a given whole slide image into tiles and processing each tile with different parameters based on local heterogeneity not only reduces the computation complexity, but also improves the analytical accuracy. Further, each whole slide image may be parsed in hierarchical fashion to access regions of the slide at different magnification levels.

Per block 208, method 200 labels each pixel in the tissue-representing portions of the whole slide images. The labeling may be performed by hand by dermatopathological specialists. The labeling may be performed using a graphical user interface that permits annotating whole slide images using standard graphical design tools, e.g., line, curve, space fill, etc.

Figure 3:
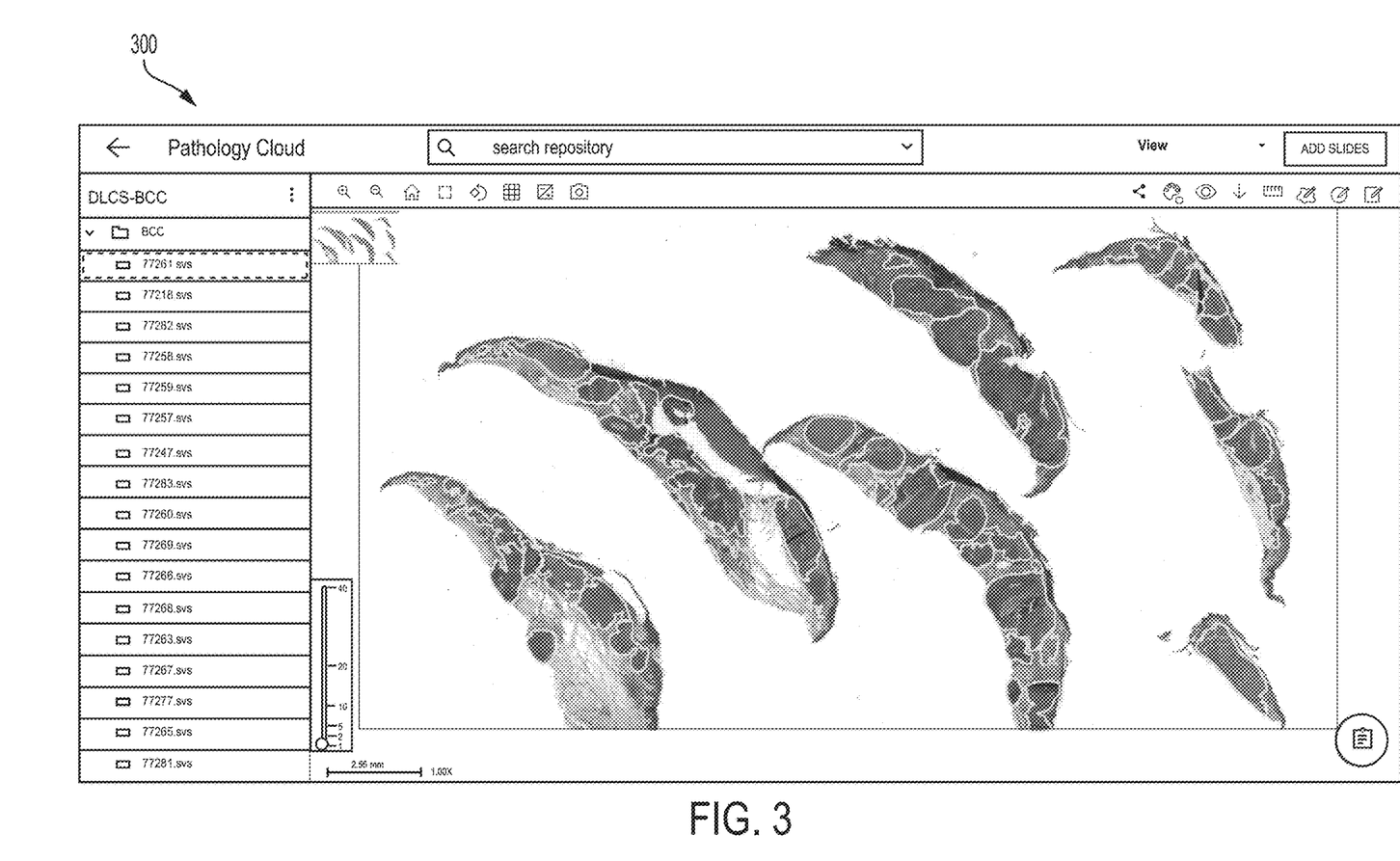
FIG. 3 depicts an expertly annotated whole slide image of several dermatopathological sections according to various embodiments.

FIG. 3 depicts an expertly annotated whole slide image 300 of several dermatopathological sections according to various embodiments. As depicted, whole slide image 300 depicts multiple sections of annotated nodular basal cell carcinoma. Annotations are depicted as white boarders to the identified portions. Annotations such as those shown on whole slide image 300 may be used per the labeling of block 208 of method 200.

At block 210, method 200 applies a binary mask to the whole slide images. The binary mask indicates delineation of normal and neoplastic or inflammatory tissue, according to the expert annotations. Distractors have no pixels with corresponding positive labels, therefore corresponding image data were tiled and produced a binary mask where all pixels were homogeneously labeled.

At block 212, method 200 trains a convolutional neural network using the whole slide images produced per blocks 202, 204, 206, 208, and 210. Suitable neural network models include 16-layer fully convolutional neural networks available from the University of Oxford Visual Geometry Group at http://www.robots.ox.ac.uk/~vgg/research/very_deep/. In the above-referenced experiments, the inventors customized such models for the dermatopathological recognition problem.

In particular, the inventors trained the experimental models by stochastic gradient descent with momentum. The learning rate was set to 10-9, 10-12, 10-13 for FCN32s, FCN16s, and FCN8s, respectively. The maximum iteration was 100,000. The inventors used momentum 0.99, weight decay 0.0005 and doubled the learning rate for biases. The class scoring convolution layer was initialized by zeros and the deconvolution layer by bilinear interpolation. The training was performed on the whole image with mini-batch one. The FCN32s net was initialized by the pre-trained fully convolutional VGG16 net. The following nets were initialized with the parameters of the last, coarser net (i.e., FCN32s→FCN16s, FCN16s→FCN8s). Thus, the inventors completely trained three deep models in sequence (FCN32s→FCN16s→FCN8s). The inventors concluded that FCN32s is likely sufficient for use in method 200. Note that some embodiments regularize each neural network model with a convergent loss function to ensure prevention of overfitting.

Once trained, the convolutional neural network models may be used for multiple purposes, including training a discriminative classifier, such as a support vector machine as shown and described below in reference to FIG. 4, or as part of a complete technique for dermatopathological analysis as shown and described below in reference to FIGS. 6 and 7.

Figure 4:
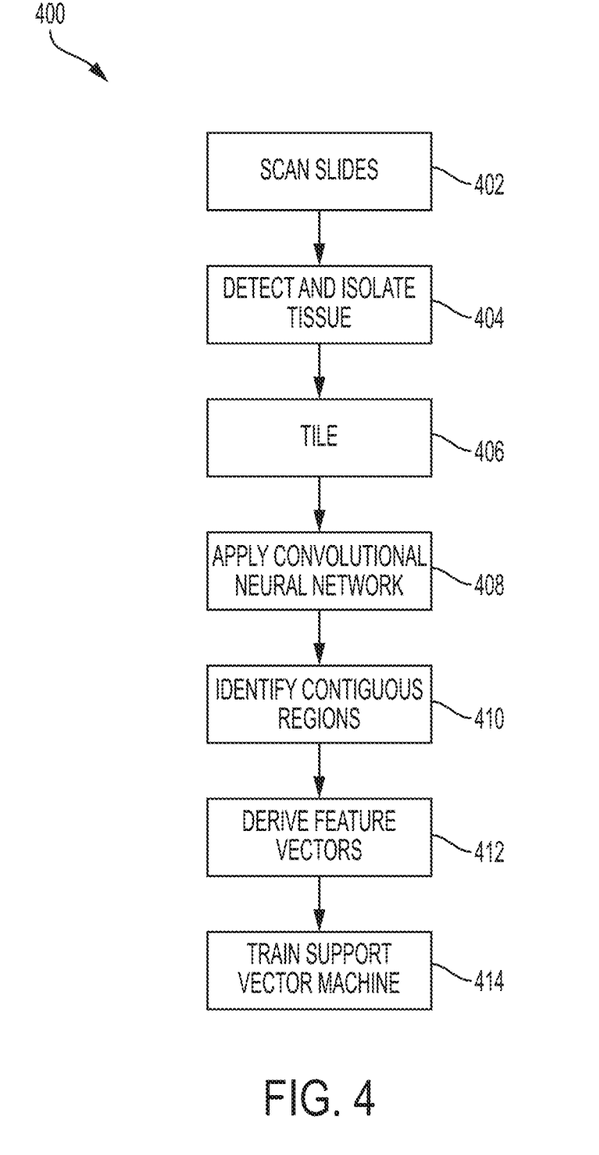
FIG. 4 is a flowchart for a method of training a discriminative classifier according to various embodiments.

FIG. 4 is a flowchart for a method 400 of training a discriminative classifier according to various embodiments. The discriminative classifier may be a support vector machine according to some embodiments. Method 400 may be implemented using a hardware computer system as shown and described below in reference to FIG. 7. Method 400 may utilize a trained convolutional neural network, such as that produced by method 200.

Per block 402, method 400 scans dermatological slides to obtain computer readable whole slide images. The actions of this block are essentially the same as the actions of block 202 of method 200. In particular, the actions of this block may be omitted and the computer readable whole slide images obtained from a different entity. The slides selected for scanning may be of essentially the same type, distribution, and quantity as described above in reference to block 202 of method 200.

Per block 404, method 400 detects and isolates tissue on the whole slide images. The actions of this block are essentially the same as the actions of block 204 of method 200.

Per block 406, method 400 tiles the whole slide images. The actions of this block are essentially the same as the actions of block 206 of method 200.

Per block 408, method 400 applies one or more trained convolutional neural networks to the whole slide images processed according to the actions of the prior blocks. The results of this block are that each whole slide image has one or more probabilities assigned to each pixel, where each probability represents the likelihood of the pixel representing a respective disease state. Such probabilities may be stored in dedicated data structures associated with the whole slide images.

Per block 410, method 400 identifies contiguous regions of high probability disease within each whole slide image (or tile, for parallelization). Such regions may be identified by selecting a threshold probability and then determining the pixels having a disease probability that exceeds the threshold. Such contiguous regions are then blob detected using known techniques.

Per block 412, each block is then used to derive a feature vector for input to a support vector machine. The vectors may represent blob size and shape, for example. That is, each detected blob is associated with an array of pixels forming its boundary and representing a simple, closed curve. From these boundary pixels, measurements such as area and perimeter can be computed, e.g., using formulas for these measures for n-sided polygons. These measurements may form components in a representational vector. Next, the vectors for each whole slide image (or tile) are combined to form a single vector for each whole slide image (respectively, tile). The vectors may be combined as described by component-wise averaging for example, i.e., constructing a vector which entries are averages taken from corresponding entries of its constituent vectors.

Per block 414, the vectors produced per block 412 are used to train a support vector machine. In particular, prior to the training, the vectors are labeled with slide-level diagnoses for input to the training phase of the support vector machine. Multiple machines may be trained, one for each disease diagnosis.

The result of method 400 is that a trained support vector machine is produced. The trained support vector machine accepts as input a specially processed output from a convolutional neural network, such as that described above in reference to FIG. 2. The trained support vector machine outputs a classification of the vector, e.g., normal versus basal cell carcinoma. Multiple support vector machines may be trained and used to classify vectors into any of a number of disease classes. The support vector machine may also output a confidence level in the output diagnosis. The confidence level may be associated with how close the classification is, e.g., how close the input vector is to the geometric hyperplane defined according to some support vector machines that partitions high dimensional space into classes.

Figure 5:
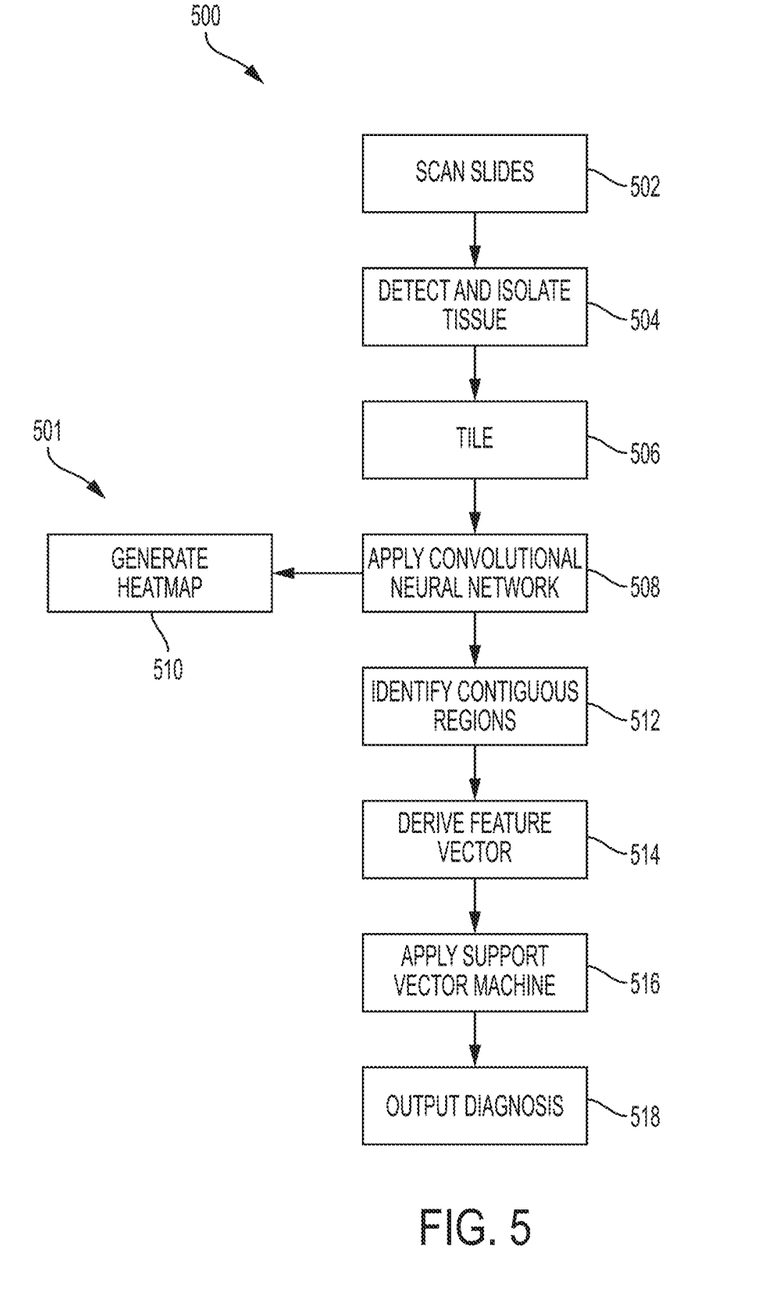
FIG. 5 is a flowchart of a method for generating a heatmap illustrating diagnosis probabilities, and for a method of at least partially automated dermatopathology using machine learning, according to various embodiments.

FIG. 5 is a flowchart of a method 500 for generating a heatmap illustrating diagnosis probabilities, and for a method 501 for at least partially automated dermatopathology using machine learning, according to various embodiments. Method 500 of generating a heatmap includes the actions of blocks 502, 504, 506, 508, and 510. Method 501 of at least partially automated dermatopathology includes the actions of blocks 502, 504, 506, 508, 512, 514, 516, and 518. Methods 500, 501 may be implemented using a hardware computer system as shown and described below in reference to FIG. 7. Method 500 is described first, followed by a description of method 502.

Per block 502, method 500 for generating a heatmap scans a dermatopathological slide. The actions of this block are essentially the same as those of block 202 of FIG. 2, except that they are performed for a single slide, or multiple slides of a single patient, where the patient's diagnosis is unknown. Like the actions of block 202, the actions of this block may be omitted and replaced by retrieving a stored whole slide image, e.g., over the internet.

Per block 504, method 500 for generating a heatmap detects and isolates tissue in the whole slide image. The actions of this block are essentially the same as those described above in reference to block 204.

Per block 506, method 500 for generating a heatmap tiles the whole slide image. The actions of this block are essentially the same as those described above in reference to block 206.

Per block 508, method 500 for generating a heat map applies a trained convolutional neural network (e.g., as described above in reference to FIG. 2) to the whole slide image (or tiles) from block 506. The result of such application is that the each pixel in the whole slide image (or tile) is labeled with a probability specific to the disease represented by the particular convolutional neural network. In other words, the whole slide image (or portion) is reconstructed with a third dimension class likelihood, which is a value representing likelihood of that pixel belonging to the given lesion.

Per block 510, method 500 for generating a heat map generates a heat map representing the probabilities assigned to individual pixels. That is, block 510 generates an image where the third dimension representing disease probability is visualized by assigning a corresponding Red-Green-Blue ("RGB") color value to represent that class likelihood. The generated heatmap is a representation of the model's ability to distinguish between benign and neoplastic or inflammatory cells within a given whole slide image (or tile). For example, visually investigative results indicate that the traditional basaloid nesting pattern in the dermis is continually identified on images where basal cell carcinoma is present.

Figure 6:
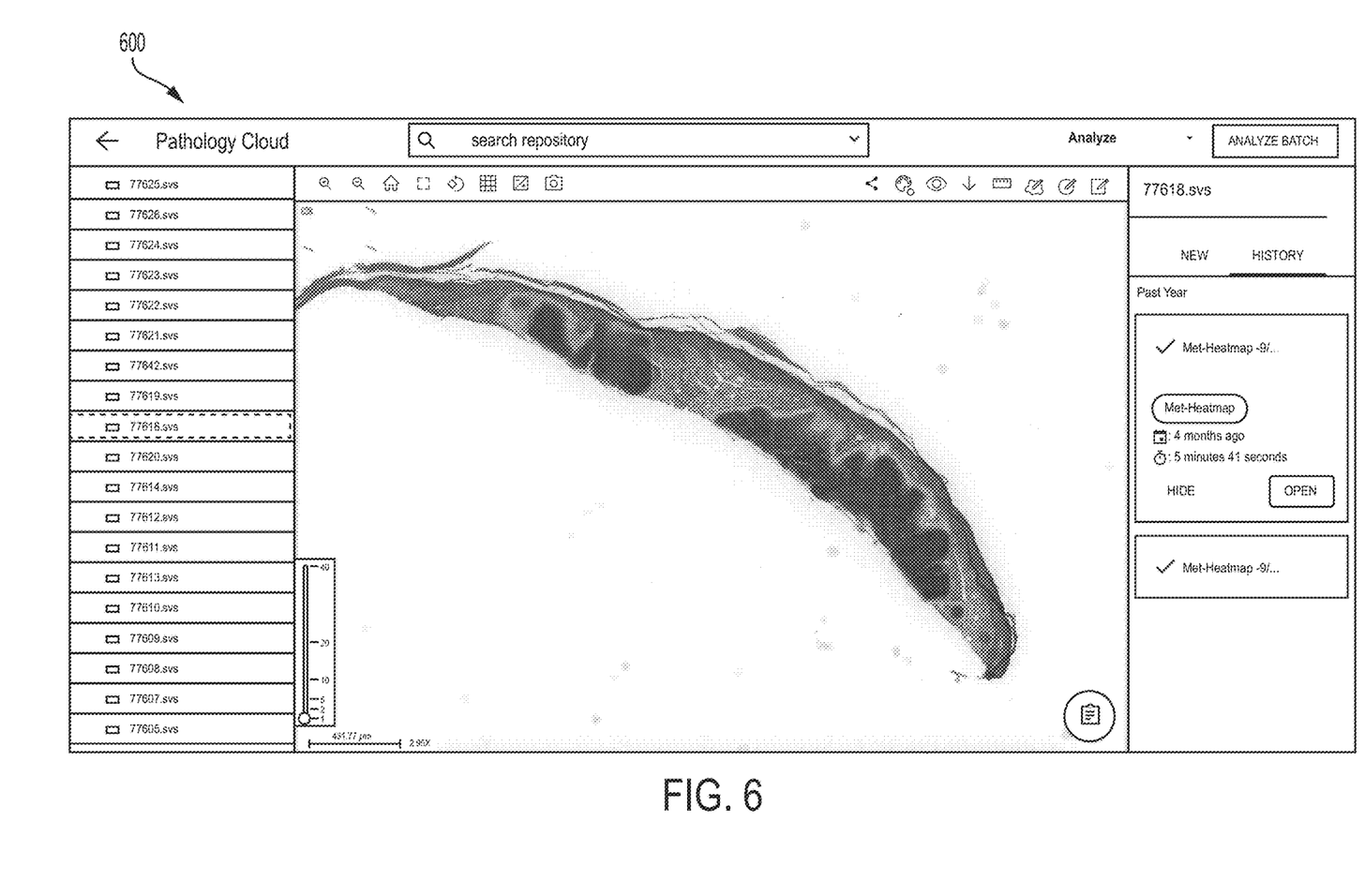
FIG. 6 depicts a heatmap depicting diagnosis probabilities according to various embodiments.

FIG. 6 depicts a heatmap 600 depicting diagnosis probabilities according to various embodiments. Heatmap 600 may be produced according to method 500 as described above. Heatmap 600 may assist in manual diagnosis by highlighting regions implicating special scrutiny for a professional dermatopathologist.

A description of method 501 for at least partially automated dermatopathology using machine learning follows below. The actions of blocks 502, 504, 506, and 508 are essentially identical to the actions of those blocks for method 500 for generating a heatmap. For method 501, the actions of block 510 are optional and may be omitted.

The actions of blocks 512 and 514 of method 501 for at least partially automated dermatopathology using machine learning are essentially the same as those described above in reference to blocks 410 and 412, respectively. The output of the actions of these blocks is a single feature vector representing the contiguous blobs of high probability disease within each whole slide image (or tile, for parallelization).

Per block 516, method 501 for at least partially automated dermatopathology using machine learning applies at least one trained support vector machine (e.g., as produced according to method 400) to the vector output per block 514. Multiple support vector machines may be employed to diagnose multiple diseases. The application of the support vector machine to the derived vector may be performed using known techniques, where the vector is input to a closed-form linear function.

Per block 518, method 501 for at least partially automated dermatopathology using machine learning outputs a diagnosis (or multiple diagnoses) provided by the support vector machine(s) of block 516. The diagnosis may be output by displaying on a computer monitor, according to some embodiments.

A user may take any of a variety of actions based on the output. According to some embodiments, the output diagnosis is displayed alongside the whole-slide image on a monitor. A human pathologist then confirms the diagnosis or issues a new diagnosis in the event of disagreement. The human-approved diagnosis may then be sent to a Laboratory Information System ("LIS"), a Laboratory Information Management System ("LIMS"), or an Electronic Medical Record ("EMR") system.

According to other embodiments, a batch of whole-slide images are processed and each is given a suggested diagnosis by the system as disclosed herein. A user then sorts the physical glass slides into folders or trays based on the suggested diagnosis performed by the system on the corresponding whole-slide images. These folders or trays of physical (glass) slides are then given to a human pathologist for confirmation of the suggested diagnoses using a microscope.

According to yet other embodiments, if diagnosis confidence level output by the support vector machine is sufficiently high, then it automatically reports its diagnosis as final to the LIS/LIMS/EMR without any human intervention. If not sufficiently confident, the case may be referred to a human pathologist for conventional review and diagnosis.

Figure 7:
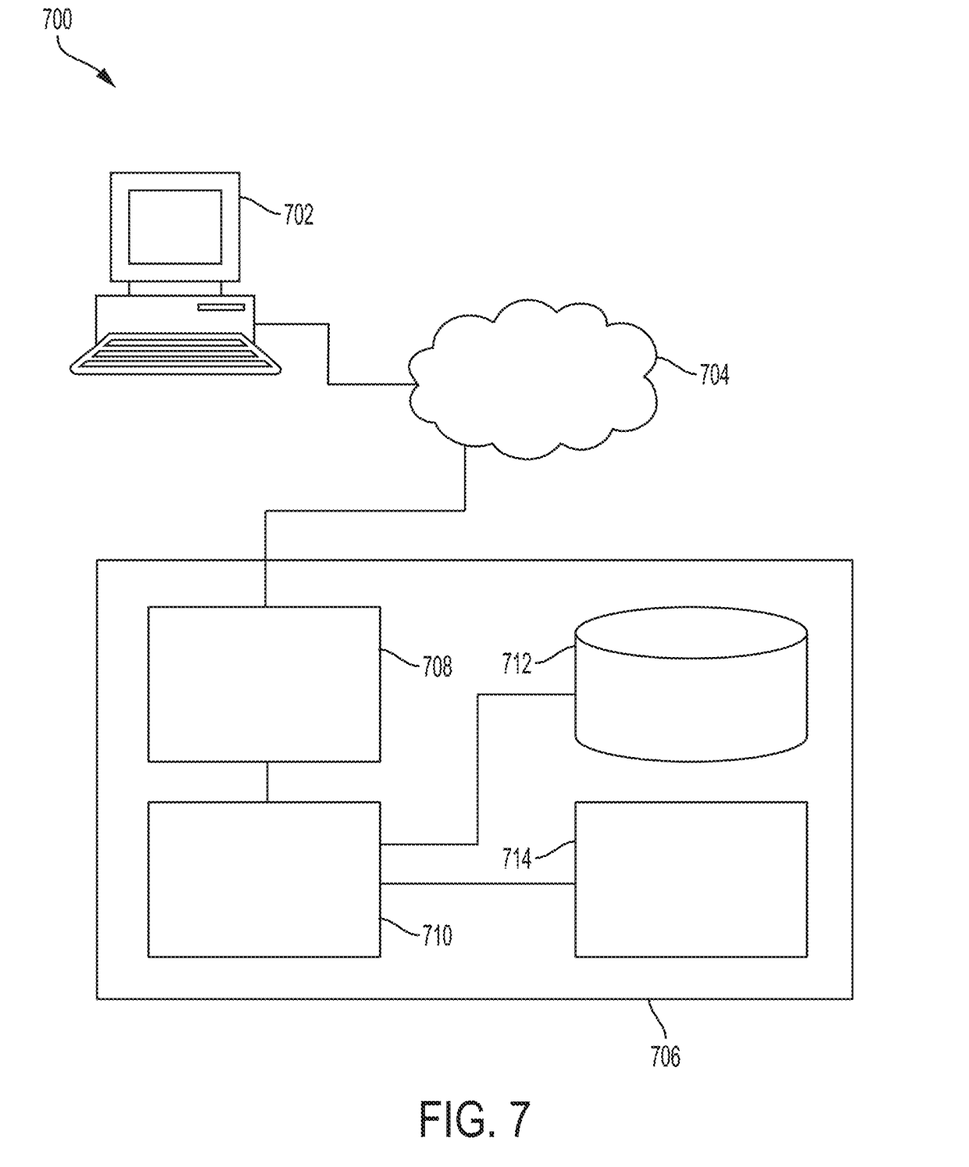
FIG. 7 is a schematic diagram depicting a system for implementing the disclosed methods according to some embodiments.

FIG. 7 is a schematic diagram of a system 700 suitable for implementation of a method as shown and described, e.g., methods 200, 400, and/or 500. System 700 may be based around an electronic hardware internet server computer 706 that includes one or more electronic processors 710, which may be communicatively coupled to the internet 704. System 700 includes network interface 708 to affect the communicative coupling to the internet 704, and, through internet 704, client computer 702. Network interface 708 may include a physical network interface, such as a network adapter. System 700 may be a special-purpose computer, adapted for reliability and high-bandwidth communications. Thus, system 700 may be embodied in a cluster of individual hardware server computers, for example. Processors 710 may be multi-core processors suitable for handling large amounts of information. In particular, processors 710 may be highly parallel. Processors 710 are communicatively coupled to persistent memory 712, and may execute instructions stored thereon to effectuate the techniques disclosed herein on concert with client computer 702 as shown and described in reference to FIGS. 2, 4, and 5 in particular.

Persistent memory 712 may be in a Redundant Array of Inexpensive Disk drives (RAID) configuration for added reliability. Processors 710 are also communicatively coupled to volatile memory 714. Volatile memory 714 may be or include Error-Correcting Code (ECC) memory hardware devices Certain examples described above can be performed in part using a computer application or program. The computer program can exist in a variety of forms, both active and inactive. For example, the computer program can exist as one or more software programs, software modules, or both, that can be comprised of program instructions in source code, object code, executable code or other formats, firmware program(s), or hardware description language (HDL) files. Any of the above can be embodied on a computer readable medium, which can include computer readable storage devices and media in compressed or uncompressed form. Exemplary computer readable storage devices and media include conventional computer system RAM (random access memory), ROM (read-only memory), EPROM (erasable, programmable ROM), EEPROM (electrically erasable, programmable ROM), and magnetic or optical disks or tapes.

Those skilled in the art will be able to make various modifications to the described examples without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. An at least partially computer implemented method of classifying human cutaneous tissue, the method comprising:
   obtaining a computer readable image of a human cutaneous tissue;
   labeling a plurality of pixels of the computer readable image, using a trained model, with at least one diagnosis probability, wherein a labeled plurality of image pixels is obtained;
   obtaining an automated diagnosis, using a trained classifier applied to at least one contiguous region of pixels defined at least in part as a portion of the labeled plurality of image pixels with a particular diagnosis probability above a predefined threshold, wherein the trained classifier is trained by tissue images and corresponding diagnostic labels, and wherein the automated diagnosis comprises at least one basaloid, squamous, or melanocytic dermatopathological condition; and
   outputting the automated diagnosis.

2. The method of claim 1, wherein the at least one dermatopathological condition comprises at least one of: basal cell carcinoma, dermal nevus, or seborrheic keratosis.

3. The method of claim 1, wherein the automated diagnosis comprises a specimen level diagnosis.

4. The method of claim 1, wherein the automated diagnosis comprises a slide level diagnosis.

5. The method of claim 1, further comprising preprocessing the computer readable image to detect and isolate image regions that represent tissue.

6. The method of claim 1, wherein the trained classifier comprises a support vector machine.

7. The method of claim 1, wherein the trained model comprises a convolutional neural network.

8. The method of claim 7, wherein the trained model is trained using stochastic gradient descent with momentum.

9. A computer system for classifying human cutaneous tissue, the computer system comprising at least one electronic processor that executes instructions to perform operations comprising:

obtaining a computer readable image of the human cutaneous tissue;

labeling a plurality of pixels of the image, using a trained model, with at least one diagnosis probability, wherein a labeled plurality of image pixels is obtained;

obtaining an automated diagnosis, using a trained classifier applied to at least one contiguous region of pixels defined at least in part as a portion of the labeled plurality of image pixels with a particular diagnosis probability above a predefined threshold, wherein the trained classifier is trained by tissue images and corresponding diagnostic labels, and wherein the automated diagnosis comprises at least one basaloid, squamous, or melanocytic dermatopathological condition; and outputting the automated diagnosis.

10. The computer system of claim 9, wherein the at least one dermatopathological condition comprises at least one of: basal cell carcinoma, dermal nevus, or seborrheic keratosis.

11. The computer system of claim 9, wherein the automated diagnosis comprises a specimen level diagnosis.

12. The computer system of claim 9, wherein the automated diagnosis comprises a slide level diagnosis.

13. The computer system of claim 9, wherein the operations further comprise preprocessing the image to detect and isolate image regions that represent tissue.

14. The computer system of claim 9, wherein the trained classifier comprises a support vector machine.

15. The computer system of claim 9, wherein the trained model comprises a convolutional neural network.

16. The computer system of claim 15, wherein the trained model is trained using stochastic gradient descent with momentum.

* * * * *